United States Patent [19]
Thurston et al.

[11] Patent Number: 5,540,226
[45] Date of Patent: Jul. 30, 1996

[54] APPARATUS FOR DETECTING CATARACTOGENESIS

[75] Inventors: George M. Thurston; George B. Benedek, both of Belmont; Douglas L. Hayden, Cambridge; Joyce A. Peetermans, Newton; Victor G. Taratuta, Boston, all of Mass.

[73] Assignee: Massachusetts Institute of Technology & Oculon Corp., Cambridge, Mass.

[21] Appl. No.: 178,874

[22] Filed: Jan. 7, 1994

Related U.S. Application Data

[62] Division of Ser. No. 637,289, Jan. 4, 1991, Pat. No. 5,279,296.

[51] Int. Cl.$^6$ ....................................................... A61B 3/00
[52] U.S. Cl. .......................................................... 128/633
[58] Field of Search ................................... 128/630–634; 606/2–4, 10–12

[56] References Cited

U.S. PATENT DOCUMENTS

| | | |
|---|---|---|
| 4,080,264 | 3/1978 | Cohen et al. . |
| 4,350,163 | 9/1982 | Ford, Jr. et al. . |
| 4,702,576 | 10/1987 | Magnante ..................................... 606/4 |
| 4,711,542 | 12/1987 | Ichihashi et al. . |
| 4,719,912 | 1/1988 | Weinberg . |
| 4,957,113 | 9/1990 | Benedek . |
| 4,993,827 | 2/1991 | Benedek et al. . |
| 5,072,731 | 12/1991 | Taratuta et al. . |

OTHER PUBLICATIONS

S. Dubin et al., "Observation of the Spectrum of Light Scattered by Solutions of Biological Macromolecules," *Proceedings of the National Academy of Sciences*, 57(5): 1164–1171 (1967).

George B. Benedek, "Optical Mixing Spectroscopy, with Applications to Problems in Physics, Chemistry, Biology and Engineering," *Polarization Matter and Radiation*, Presses Universitaires, Paris, pp. 49–84, (1969).

N. Clark et al., "A Study of Brownian Motion Using Light Scattering," *American Journal of Physics*, 38(5):575–585, (1970).

T. Tanaka and G. Benedek, "Observation of protein diffusivity in intact human and bovine lenses with application to cataract," *Investigative Ophthalmology*, 14(6):449–456 (1975).

J. Jedziniak et al., "The Concentration and Localization of Heavy Molecular Weight Aggregates in Aging Normal and Cataractous Human Lenses," *Exp. Eye Res.*, 20:367–369, (1975).

T. Tanaka and C. Ishimoto, "In vivo observation of protein diffusivity in rabbit lenses," *Invest. Ophthalmol. Visual Sci.* 16(2):135–140 (1977).

J. Jedziniak et al., "Quantitative verification of the existence of high molecular weight protein aggregates in the intact normal human lens by light-scattering spectroscopy," *Invest. Ophthalmol. Visual Sci.*, 17(1):51–57 (1978).

J. Clark and G. Benedek, "Phase Diagram for Cell Cytoplasm from the Calf Lens," *Biochemical and Biophysical Research Communications*, 95(1):482–489 (1980).

M. Dalaye et al., "Identification of the Scattering Elements Responsible for Lens Opacification in Cold Cataracts," *Biophys. J.* 37:647–656 (1982).

(List continued on next page.)

*Primary Examiner*—David M. Shay
*Attorney, Agent, or Firm*—Seed and Berry LPP

[57] ABSTRACT

An apparatus is disclosed for using quasielastic light scattering to determine the degree of cataractogenesis of a lens in vivo. By collecting and analyzing light scattered from the lens, it is possible, using the temporal autocorrelation function, to produce a signature of cataractogenesis, accounting for scattering due to immobile scatterers. The components of the cataractogenesis can also be detected by comparing the values of the components of the signature of cataractogenesis to frequency distribution of the components taken from populations or by detecting changes in the values of the components of the signature of cataractogenesis as a function of time.

21 Claims, 16 Drawing Sheets

OTHER PUBLICATIONS

I. Nishio et al., "In Vivo Observation of Lens Protein Diffusivity in Normal and X–Irradiated Rabbit Lenses," *Exp. Eye Res.* 39:61–68 (1984).

R. Zeimer and J. Noth, "A New Method of Measuring in vivo the Lens Transmittance, and Study of Lens Scatter, Fluorescence and Transmittance," *Ophthalmic Res.* 16:246–255 (1984).

R. A. Weale, "Human Lenticular Fluorescence and Transmissivity, and their Effects on Vision," *Exp. Eye Research, 41:457–473 (1985).*

T. Libondi et al., "*In vivo* measurement of the aging rabbit lens using quasielastic light scattering," *Current Eye Research,* 5(6):411–419 (1986).

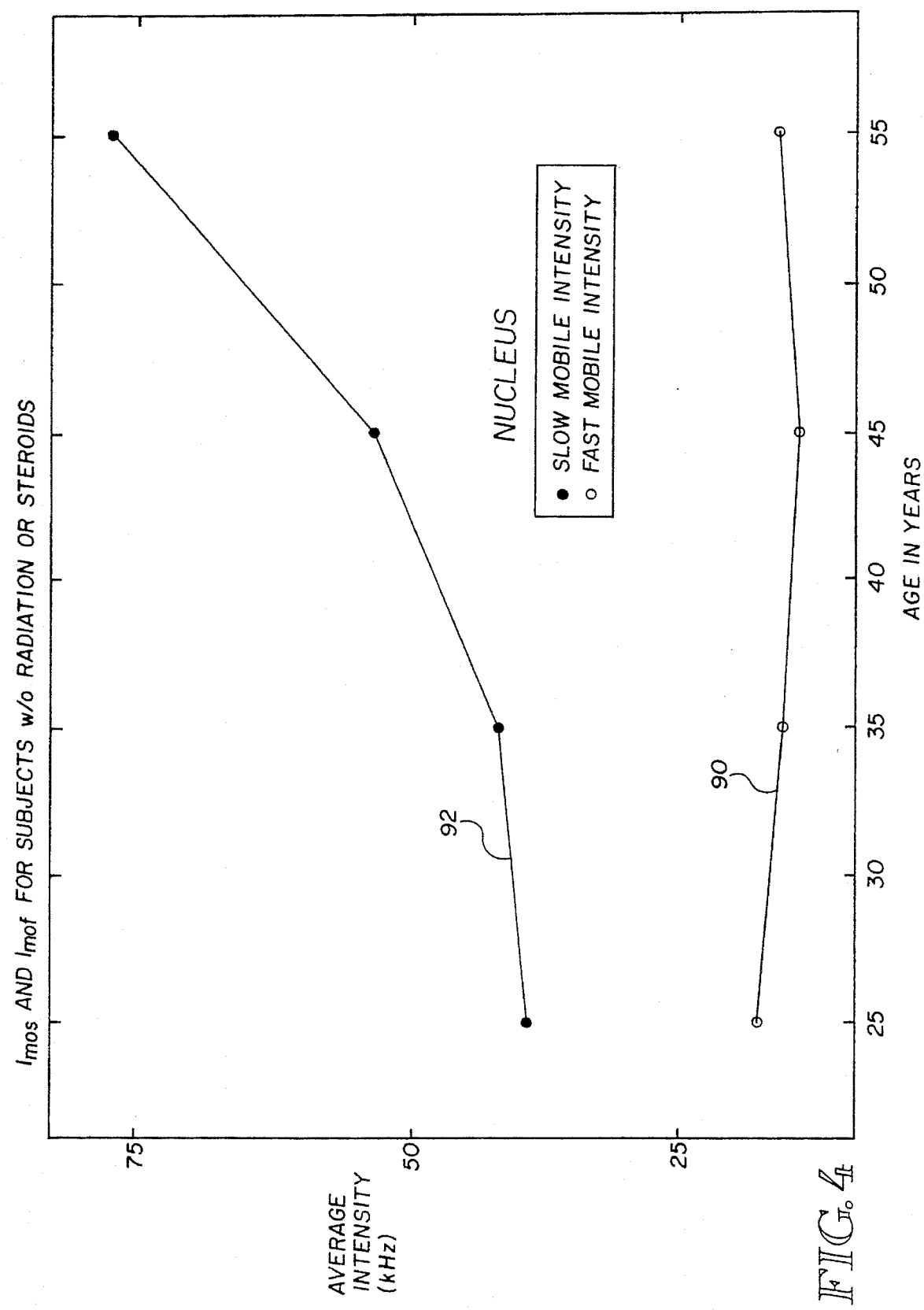

APPARATUS FOR DETECTING CATARACTOGENESIS

This invention was made with government support under grant number NIH-5RO1-EY05127 awarded by the National Institutes of Health. The government has certain rights in the invention.

CROSS-REFERENCE TO RELATED APPLICATION

This application is a division of U.S. patent application Ser. No. 07/637,289, filed Jan. 4, 1991, now U.S. Pat. No. 5,279,296.

TECHNICAL FIELD

The present invention relates to a method and apparatus for detecting diseases, and more particularly, to a method and apparatus for detecting diseases by inspecting ocular tissue.

BACKGROUND OF THE INVENTION

A reliable, quantitative and noninvasive method for the characterization of the molecular changes associated with early cataractogenesis in vivo has long been an important goal of human clinical cataract research. Such a method would allow researchers and physicians to (a) assess the effectiveness of putative anticataract reagents; (b) evaluate the cataractogenic role of pharmacologic agents or radiation used in the treatment of systematic diseases; (c) characterize early cataract in epidemiologic studies of human or animal populations subject to differential cataractogenic stress; and (d)provide a quantitative basis for the medical decision to intervene surgically or pharmaceutically in the treatment of cataract.

In 1975, T. Tanaka and G. Bencrick ("Observation of Protein Diffusivity in Intact Human and Bovine Lenses with Application to Cataract," *Invest. Opthal*, 14, 1985, pp. 449–456) showed that the Brownian motion of proteins in excised human and bovine lenses could be measured optically using the method of quasielastic light scattering (QLS) spectroscopy. Following this work, T. Tanaka and C. Ishimoto ("In Vivo Observation of Lens Protein Diffusivity in Normal and X-Irradiated Rabbit Lenses," *Exp. Eye Res.*, 39, 1984, pp. 61–68) demonstrated that QLS could be used in vivo in the rabbit to detect changes in mean protein diffusivity as a function of age and position in the lens. Further observations showed that the cataractogenic insult of x-irradiation upon the rabbit lens produced dramatic changes in the form of the autocorrelation function of the scattered light at a very early stage in the cataractogenic process. The autocorrelation function is an important tool for mathematical analysis of QLS. This change in the autocorrelation function demonstrated that the x-irradiation was responsible for drastic changes in the diffusivity of the protein scattering elements undergoing Brownian movement within the ocular tissue. Both Nishio and the 1977 Tanaka team observed that these altered correlation functions had a form different from that expected for the Brownian motions of a single-type scatterer. However, neither understood a quantitative analysis of the information contained in the non-exponential character of the autocorrelation function observed.

In 1986, T. Libondi et al. ("In Vivo Measurement of the Aging Rabbit Lens Using Quasielastic Light Gathering," *Curr. Eye. Res.*, Vol. 5, No. 6, 1986, pp. 411–419) showed that the form of the autocorrelation function of the scattered light from a living rabbit eye indicated the presence of at least two distinct diffusing aspects within the rabbit lens. One species had a diffusivity corresponding to the α-crystalline protein. The other was a much more slowly diffusing species of the type discovered in vitro by M. Delaye et al. ("Identification of the Scattering Elements Responsible for Lens Opacification in Cold Cataracts," *Biophys. J.*, 37, 1982, pp. 647–656).

A recently discovered method of cataract detection comprises irradiating a measurement location of a lens with a laser and collecting the light scattered from the lens at the measurement location. The collected light is then analyzed using an autocorrelator or spectrum analyzer to determine the relative amount of light scattered from different protein scatterers in the lens, and the relative light data are analyzed to determine the degree of cataract formation at the measurement location in the lens. A more detailed description of the method is given in U.S. Pat. No. 4,957,113, issued Sep. 18, 1990, which is incorporated herein by reference. However, in situations where the lens contains a significant amount of immobile protein species, this method is not suitable.

SUMMARY OF THE INVENTION

It is an object of the present invention to provide an apparatus for detecting cataractogenesis that account for the presence of immobile scatterers at the measurement location of ocular tissue.

It is another object of the present invention to provide an apparatus that can detect cataractogenesis in an individual subject in an in vivo manner through the comparison of the value of one or more variables measured in the individual to a frequency distribution of the same variables in a population of subjects.

It is a further object of the present invention to provide an apparatus that can detect cataractogenesis in an individual subject in an in vivo manner through the detected change of the value of one or more variables measured in the individual.

The present invention provides apparatus for in vivo detection of cataractogenesis. More specifically, a laser is used to provide a low-power, coherent, and uniform beam of light which is guided to a measurement location in the eye of a subject for scattering by ocular protein molecules. The scattered light is viewed, and a portion of it is collected. The intensity of the light scattered by the measurement location and the fluctuations of the intensity of the scattered light are analyzed mathematically, thereby determining a signature of cataractogenesis, the signature including the intensity ($I_{imm}$) of the light scattered by immobile scatterers at the measurement location in the ocular tissue. The degree of cataractogenesis is determined from the signature of cataractogenesis.

The present invention pertains to an apparatus for in vivo detection of cataractogenesis in ocular tissue, comprising:

a light source producing a substantially monochromatic, coherent, collimated light;

optics directing the light to impinge on the ocular tissue;

a light collector for collecting light that is scattered from the ocular tissue, the scattered light having a fluctuating intensity;

electrical circuitry performing a mathematical analysis on the intensity and the fluctuations of the intensity of the collected light, thereby determining a signature of cataractogenesis, the signature including the intensity ($I_{imm}$) of the light scattered by immobile particles in the ocular tissue; and electrical circuitry determining from the signature the degree of cataractogenesis.

The above and other features of the invention, including various novel details of combination of pans, will now be more particularly described and pointed out in the claims. It will be understood that the particular cataractogenesis detection apparatus embodying the invention is shown by way of illustration only, and not as limitations of the invention. The principles and features of this invention may be employed in various and numerous embodiments without departing from the spirit and scope of the invention.

BRIEF DESCRIPTION OF THE DRAWINGS

FIG. 4 is a graph of the average intensity of slow moving particles and fast moving particles in subjects without radiation or steroids, as a function of age, group.

DETAILED DESCRIPTION OF THE INVENTION

Figure 1:
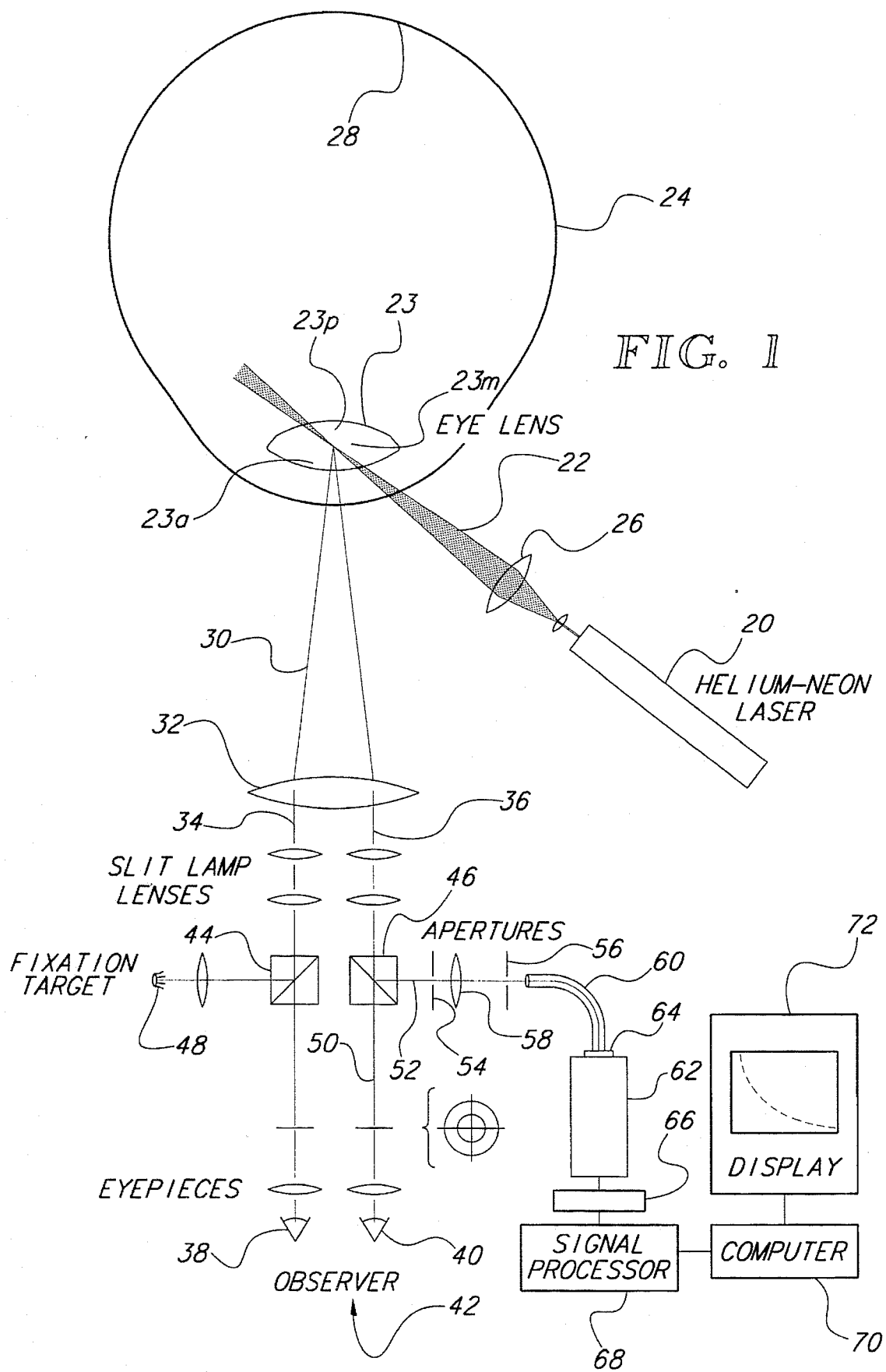
FIG. 1 is a schematic representation of an optical scattering analyzer for the study of the intensity and temporal fluctuations of the intensity of laser light scattered from the lens in vivo.

The proteins present in ocular tissue undergo random diffusive movement due to continuous collisions with nearby molecules. When a coherent, steady beam of light is scattered by the moving proteins, the intensity of the scattered light fluctuates in time. The movements of the proteins determine the rate of intensity fluctuation. It has been determined that small proteins generally diffuse faster than larger proteins or protein aggregates, while immobile proteins do not diffuse at all. Thus, it is possible to examine the intensity and fluctuations in intensity to determine the relative intensity of light scattered from the small or fast moving protein species, the large or slow moving protein species and the immobile protein species within the lens tissue. It is also possible to determine thee relative amounts of these three species and the diffusivities of the two mobile species.

The aggregation of small proteins within the lens is the very first stage in the process of cataractogenesis. By using information obtained from the light scattered by the various fast and slow moving and immobile protein species, it is possible to interpret, in a clear and unambiguous manner, the meaning of the components contained in the autocorrelation function. This invention permits the decoding of the information contained in the random intensity fluctuations in the light scattered from the lens. The decoded information has been shown clinically to provide an accurate quantitative measure of cataract development on a molecular level long before it could be detected visually by either the subject or the physician.

Brownian motion is defined as the motion of macromolecules caused by thermal agitation and the random striking by neighboring molecules in a solution. In the lens of the human eye, protein molecules undergoing Brownian motion may be recorded and analyzed by quasielastic light scattering.

In quasielastic light scattering (QLS), the temporal fluctuations in intensity of light scattered by a selected small volume in the lens which is illuminated by an incident laser beam are studied. The scattered light intensity fluctuates in time because of the Brownian motion of the scattering elements. In the case in which the laser beam illuminates the lens of the eye, the scattering elements are the molecular constituents of the fiber cells within the lens. These constituents are principally globular proteins called crystallins.

The light intensity fluctuations are detected by collecting the light scattered from a well-defined, illuminated volume in the eye lens and focusing this light onto the surface an optical square law detector such, as a photomultiplier tube or solid-state photodiode. The output of the detector is a photoelectric current whose temporal fluctuations are synchronized with the fluctuations in the scattered light intensity. The temporal fluctuations in the photocurrent can be analyzed mathematically by obtaining the autocorrelation function of the photocurrent. From the mathematical form of the autocorrelation function of the photocurrent, it is possible to determine the diffusivity of the scattering elements undergoing Brownian movement.

The autocorrelation function may be determined by using an autocorrelator to analyze the fluctuations in the intensity of the laser light scattered by the ocular tissue. The random motions of the crystalline proteins within the lens give rise to concentration fluctuations, which in turn give rise to fluctuations in the intensity of the scattered light This scattered light may be recorded in the form of a time correlation function, the autocorrelation function $C(\tau)$, which relates the scattered light intensity at a time t, I(t), to the intensity a certain time $\tau$ later, I(t+$\tau$), as follows: $C(\tau)=<I(t)I(t+\tau)>$, where $<>$ denotes averaging over all starting times t.

The photocurrent temporal autocorrelation function will have a general form which can be expressed as follows:

$$C(\tau)=\alpha_0[I_{mo}f(\tau)]^2+[I_{mo}+I_{imm}]^2, \quad (1a)$$

where $\tau$ is a time delay variable, $\alpha_0$ is a predetermined constant representative of scattering in the absence of immobile particles, and $f(\tau)$ is a monotonically decreasing positive function in $|\alpha|$ such that $f(0)=1$ and $f(\tau) \to 0$ as $|\tau| \to \infty$.

In this equation, $I_{mo}$ is the intensity of light scattered from the mobile protein species or particles within the ocular tissue, and $I_{imm}$ is the intensity of light scattered from the immobile protein species or particles in the ocular tissue.

In a less general form, the photocurrent temporal autocorrelation function can be expressed as:

$$C(\tau)=\alpha_0 [I_{mof}exp(-\tau/\tau_f)+I_{mos}exp(-\tau/\tau_s)]^2+[I_{mof}+I_{mos}+I_{imm}]^2, \quad (1b)$$

where $\tau$ is a time delay variable, and $\alpha_0$ is a predetermined constant representative of scattering in the absence of immobile particles. $I_{mof}$ is the intensity of light scattered from the fast diffusing protein species or particles within the ocular tissue, $I_{mos}$ is the intensity of light scattered from the slow diffusing mobile protein species or particles in the ocular tissue, and $I_{imm}$ is the intensity of light scattered from the immobile protein species or particles within the ocular tissue. $\Gamma_f=1/\tau_f=D_fK^2$ is the decay rate of the fast diffusing species, and $\Gamma_s=1/\tau_s=D^sK^2$ is the decay rate of the slow diffusing species. $D_f$ and $D_s$ are the diffusivities of the fast and slow species, respectively. $K=(4\pi n/\lambda)\sin(\theta/2)$ is the scattering vector where n is the index of refraction of the lens, $\lambda$ is the wavelength of the laser in vacuo, and $\theta$ is the scattering angle.

The first step in the analysis is to take the experimental measurements of $C(\tau)$ and to fit it to the mathematical form represented in Equation (1a) or Equation (1b). This mathematical fitting procedure is carried out in the computer using one of a amber of well established fitting routines. It should be noted that, in general, more than two exponentials may in fact be contained in $C(\tau)$. However, because of the limited signal-to-noise ratio which results from a clinically desirable short measurement time (approximately 1–3 sec.), the correlation function could be fit quite satisfactorily to Equation (1) or Equation (2). As a result of the fitting procedure, one deduces the fundamental parameters $I_{mof}$ and $I_{mos}$ and their sum $I_{mof}+I_{mos}=I_{mo}$.

Turning now to the Figures, FIG. 1 is a schematic representation of an optical scattering analyzer for the study of the temporal fluctuations of laser light scattered from a lens in vivo. In FIG. 1, a source of substantially monochromatic, coherent, collimated light 20, such as a laser, delivers a light beam 22, to the lens 23 of a subject's eye 24, through a delivery means, which may consist of, for example, a focusing lens 26 which serves to focus the light beam 22 onto the subject's eye 24 at the specific location at which the measurement is to be taken. The light must be focused for two reasons. First, the size of the illuminated area is inversely proportional to the coherence area of the scattered light. By focusing onto a small area, a greater coherence area is obtained which allows easier measurement. Second, the incident contact area on the lens 23 is inversely proportional to the scattering area on the retina 28. There are three areas of the lens 23 that are of particular interest. They are the anterior cortex 23a, the posterior cortex 23p and the nucleus 23n. By focusing on the lens 23, the light going to the retina 29 is diffused, thereby preventing retinal damage. Scattered light 30 from the eye lens 23 passes through a collector 32 such as an objective lens. The scattered light 30 is split into two light beams 34 and 36, which are respectively directed to the left and right eyes 38 and 40 of an observer 42. The light beams 34 and 36 respectively pass through beam splitters 44 and 46. Part of the beam 34 is directed toward the fixation target 48, which is intended to fix the position of the individual subject's eye 24 as measurements are being made. The remainder of the beam that is split by the beam splitter 44 is directed toward the left eye 38 of the observer 42.

The light beam 36 is split by the beam splitter 46 into one portion 50 which passes directly to the right eye 40 of the observer 42 and a second portion 52 which passes through apertures 54 and 56, and is focussed by the lens 58 onto the end of the optical fiber 60. The apertures 54 and 56 limit the length of the light beam 52. The optical fiber 60 directs the light beam 52 to an optical square law detector 62, such as a photomultiplier tube or solid-state photodiode, after passing through an optical filter 64. The light passing into the optical square law detector 62 is converted into a photoelectric signal through the optical filter 64, such as a photomultiplier tube or solid-state photodiode. The signal from the optical square law detector 62 is pre-processed by a preamplifier and discriminator 66. This signal is then inputted into a signal processor 68 (which can be a standalone autocorrelator or a programmed computer), and a computer 70 for processing as discussed previously. The computer 70 can be a programmed microprocessor on an integral circuit The autocorrelation function and any calculated parameters can be shown on a display 72.

Figure 2A:
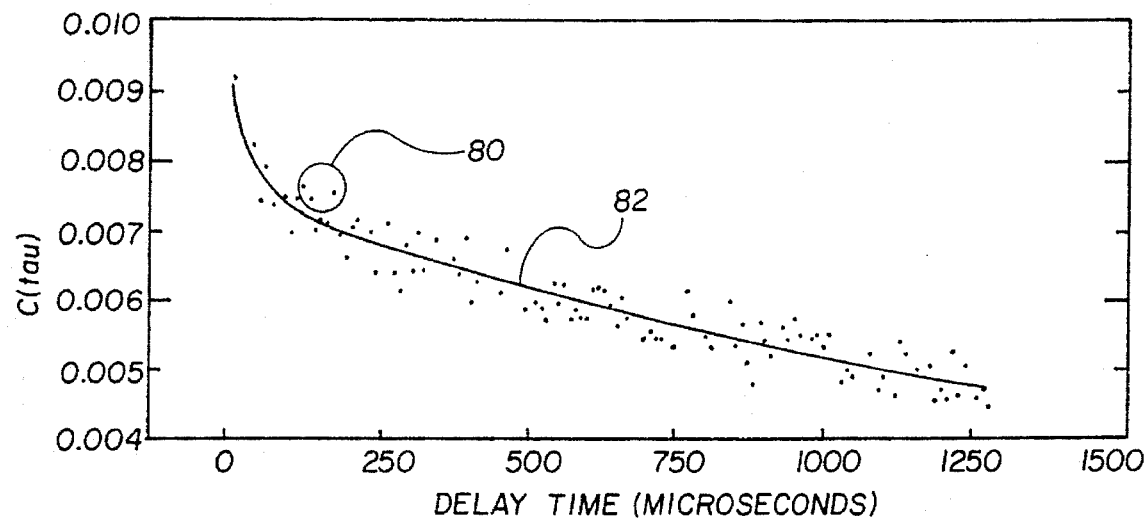
FIG. 2A is graph of a typical measured temporal autocorrelation function and a best fitting functional form, as functions of delay time.

FIG. 2A is a graph of a typical measured temporal autocorrelation function and a best fitting functional form, as functions of delay time. The data comprising the measured temporal autocorrelation function are represented by the points 80, and the best fitting functional form is indicated by the curve 82. The general trend of the measured temporal autocorrelation function is to decrease from a maximum value at zero delay time, and the curve 82 is strictly monotonically decreasing as a function of the delay time. The general forms of temporal autocorrelation functions given above exhibit these characteristics.

Figure 2B:
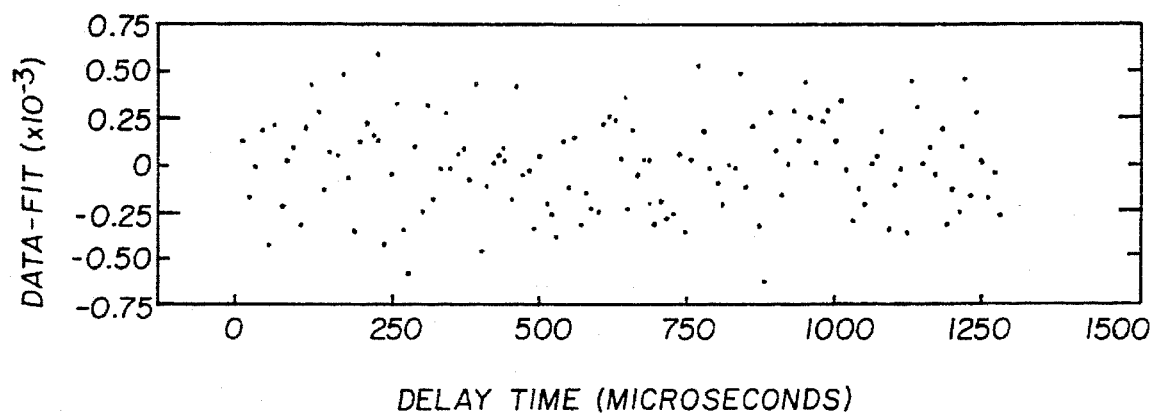
FIG. 2B is a graph of the residual differences between the measured temporal autocorrelation function and the best fitting function form as a function of delay time.

FIG. 2B is a graph of the residual between the measured temporal autocorrelation function and the best fitting functional form, as shown in FIG. 2A as a function of delay time. The residual data appear to be uniformly distributed about zero, independently of delay time. If any trend were apparent in the residual data, the quality of the fit of the curve 82 to the data represented by the points 80 would be suspect. The best fitting functional form can be determined by standard curve-fitting techniques, such as the least squares method.

Figure 3A:
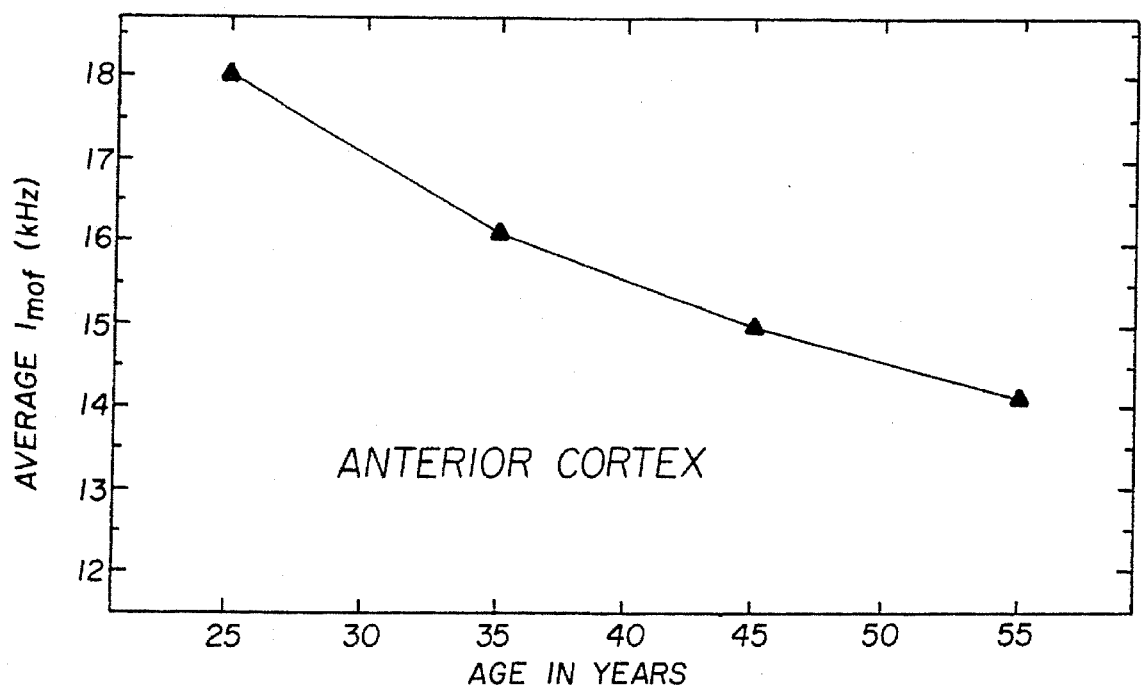
FIG. 3A is a graph of the average intensity of light scattered by fast moving particles from the anterior cortex of the lenses of subjects without radiation or steroids, as a function of age group.

FIG. 3A is a graph of the average intensity of light scattered by fast moving particles from the anterior cortex of the lenses of subjects who have not been subjected to radiation treatment or steroids, as a function of age group. The four age groups are for individuals between (a) 20 and 30 years of age, (b) 30 and 40 years of age, (c) 40 and 50 years of age, and (d) 50 and 60 years of age. The trend for this average intensity to decrease with increasing age is apparent, indicating that, on average, the number density of fast moving particles in the anterior cortex also decreases with age.

Figure 3B:
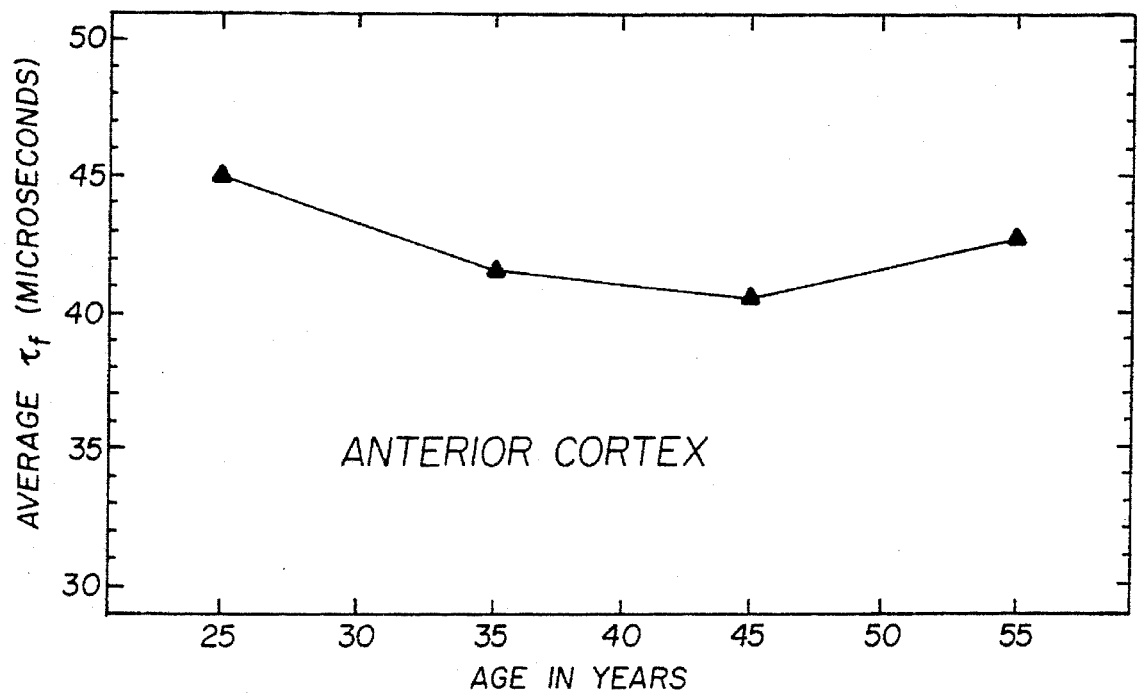
FIG. 3B is a graph of the average diffusion delay of time for fast moving particles from the anterior cortex of the lenses of subjects without radiation or steroids, as a function of age group.

FIG. 3B is a graph of the average diffusion delay time for fast moving particles from the anterior cortex of the lenses of subjects who have not been subjected to radiation treatment or steroids, as a function of age group. The average diffusion delay time for fast moving particles tends to remain between about 40 and 45 microseconds, indicating that diffusion delay time for fast moving particles in the anterior cortex is not a strong function of age.

FIG. 4 is a graph of the average intensity of light scattered by slow moving particles and fast moving particles in the lenses subjects who have not been subjected to radiation treatment or steroids, as a function of age group. The curve 90 represents the average intensity of light scattered by fast moving particles, and the curve 92 represents the average intensity of light scattered by slow moving particles. It is apparent that the average intensity of light scattered by slow moving particles increases as a function of age group and that the average intensity of light scattered by fast moving particles is relatively constant compared to that for light scattered by slow moving particles.

Figure 5:
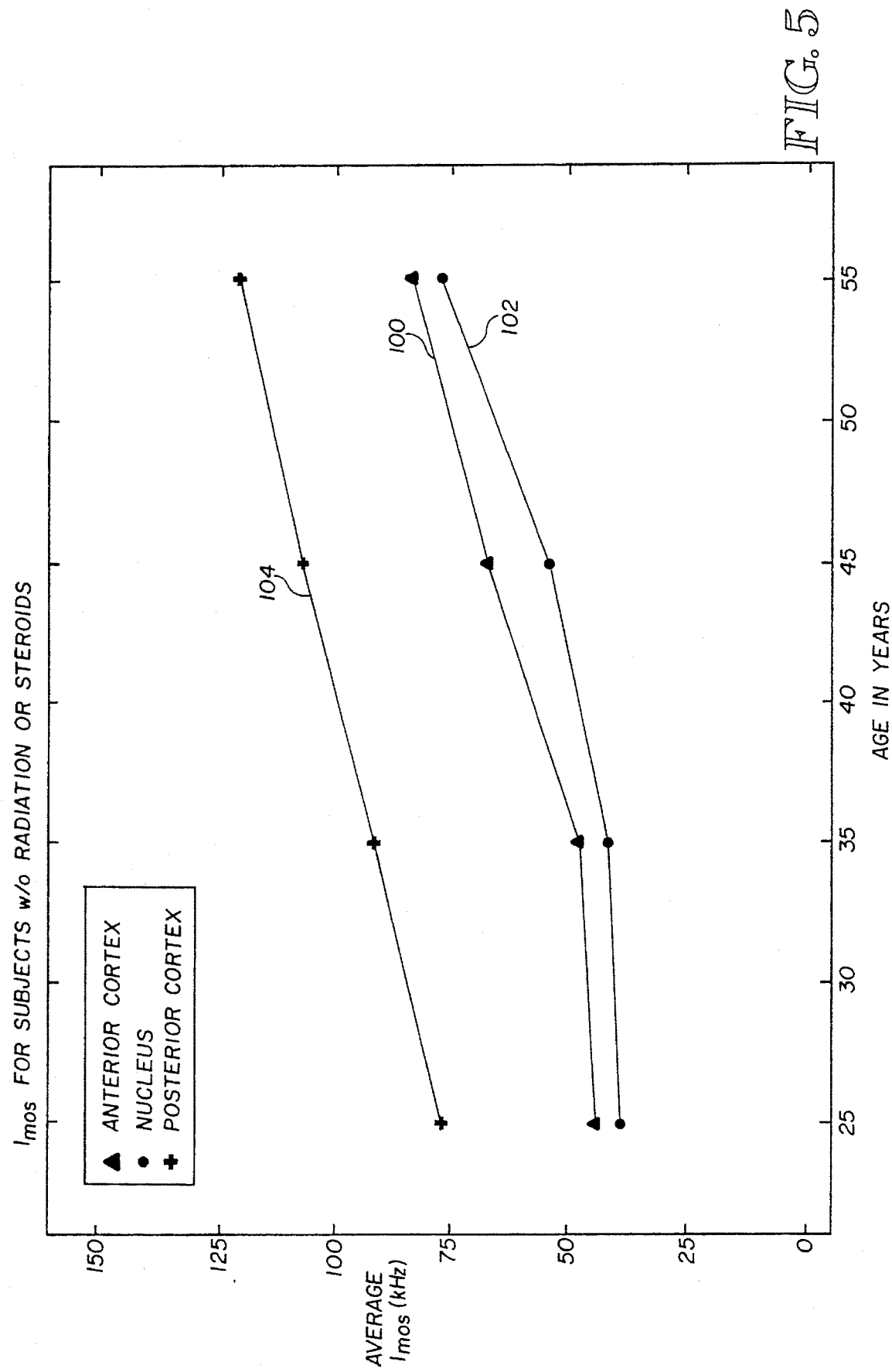
FIG. 5 is a graph of the average intensity of slow moving particles at various locations in the lens for subjects without radiation or steroids, as a function of age group.

FIG. 5 is a graph of the average intensity of light scattered by slow moving particles at various locations in the lenses of subjects who have not been subjected to radiation treatment or steroids, as a function of age group. Curves 100 and 102, respectively representing scattering from the anterior cortex and the nucleus of the subject's eyes, have magnitudes that are smaller than the magnitude of the scattering due to slow moving particles in the posterior cortex of the eye, as represented by the curve 104.

Figure 6:
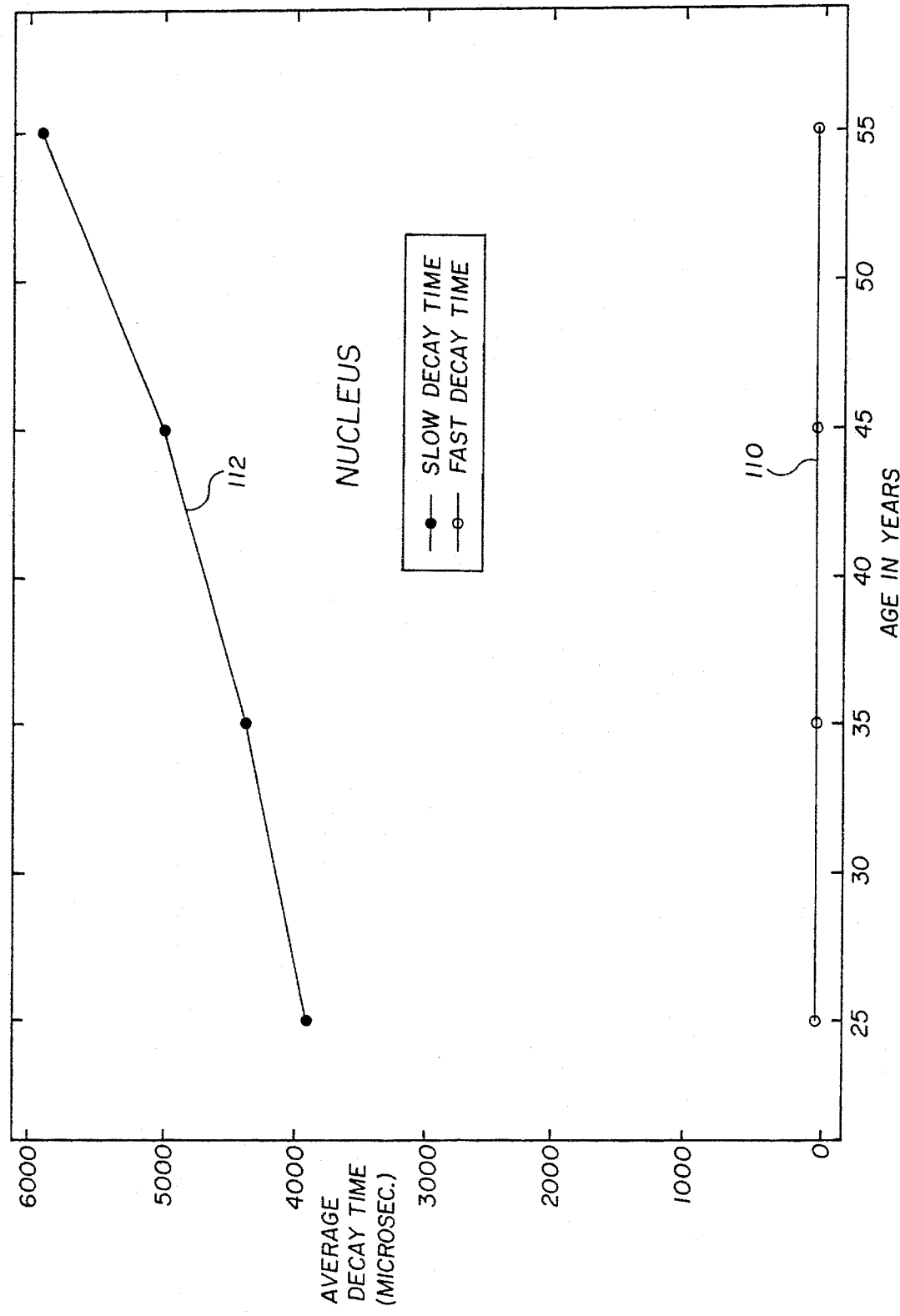
FIG. 6 is a graph of the average decay time for slow and for fast moving particles in subjects without radiation or steroids, as a function of age group.

FIG. 6 is a graph of the average decay time for slow and for fast moving particles in the lenses of subjects who have not been subjected to radiation treatment or steroids, as a function of age group. The curve 110 represents the average decay time of Light scattered by fast moving particles, and the curve 112 represents the average decay time of light scattered by slow moving particles. It is apparent that the average decay time of light scattered by slow moving particles increases as a function of age group and that the average decay time of light scattered by fast moving particles is relatively constant compared to that for light scattered by slow moving particles. Our data show that just as $I_{mos}$ increases with age, so too does $\tau_s$. This has two likely molecular origins: (1) an increase in the size of the slow mobile scattering particles with age, and (2) an increase in the viscosity of the ocular lens cytoplasm. In any case, the measurement of $\tau_s$ can provide another signature of the process of cataractogenesis. It is also possible that $\tau_s$ can provide a signature of the progressive hardening of the lens associated with presbyopia.

Figure 7:
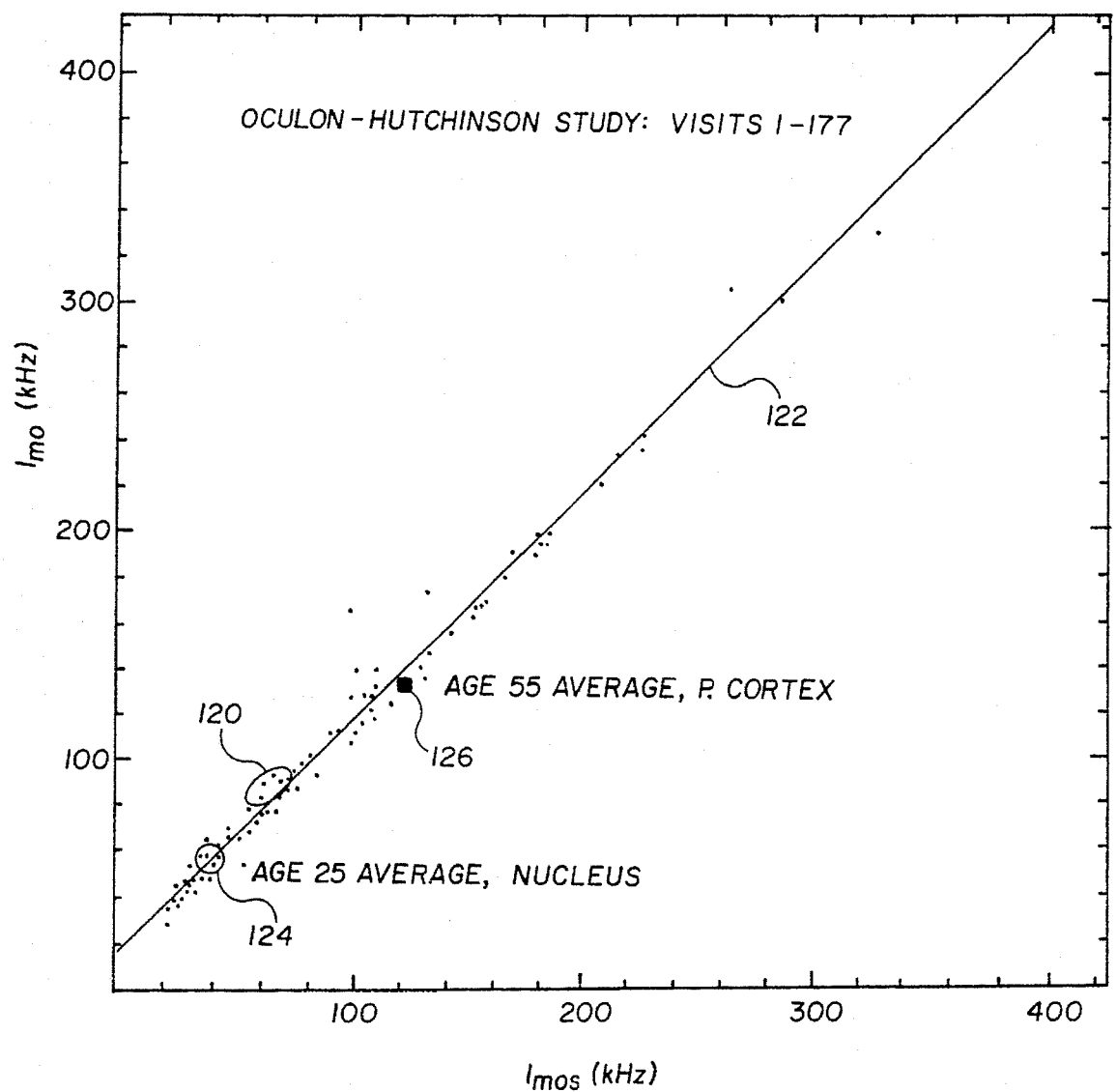
FIG. 7 is a graph of the dependence of the average intensity of scattering due to mobile particles as a function of the average intensity of scattering due to slow moving particles in the human ocular lens.

FIG. 7 is a graph of the dependence of the average intensity of scattering due to mobile particles as a function of the average intensity of scattering due to slow moving particles in the human ocular lens. The data are represented by the points 120 and the best fitting curve 122 is the universal curve which represents the locus followed by a subject who is experiencing cataractogenesis. The farther the point determined by the intensities of light scattered from mobile and slow moving particles moves from the origin, the higher the degree of cataractogenesis. For example, point 124 represents the average data for scattering from the nucleus of subjects in the 20-to-30-year age group, while point 126 represents the average data for scattering from the posterior cortex of subjects in the 50-to-60-year age group.

Figure 8:
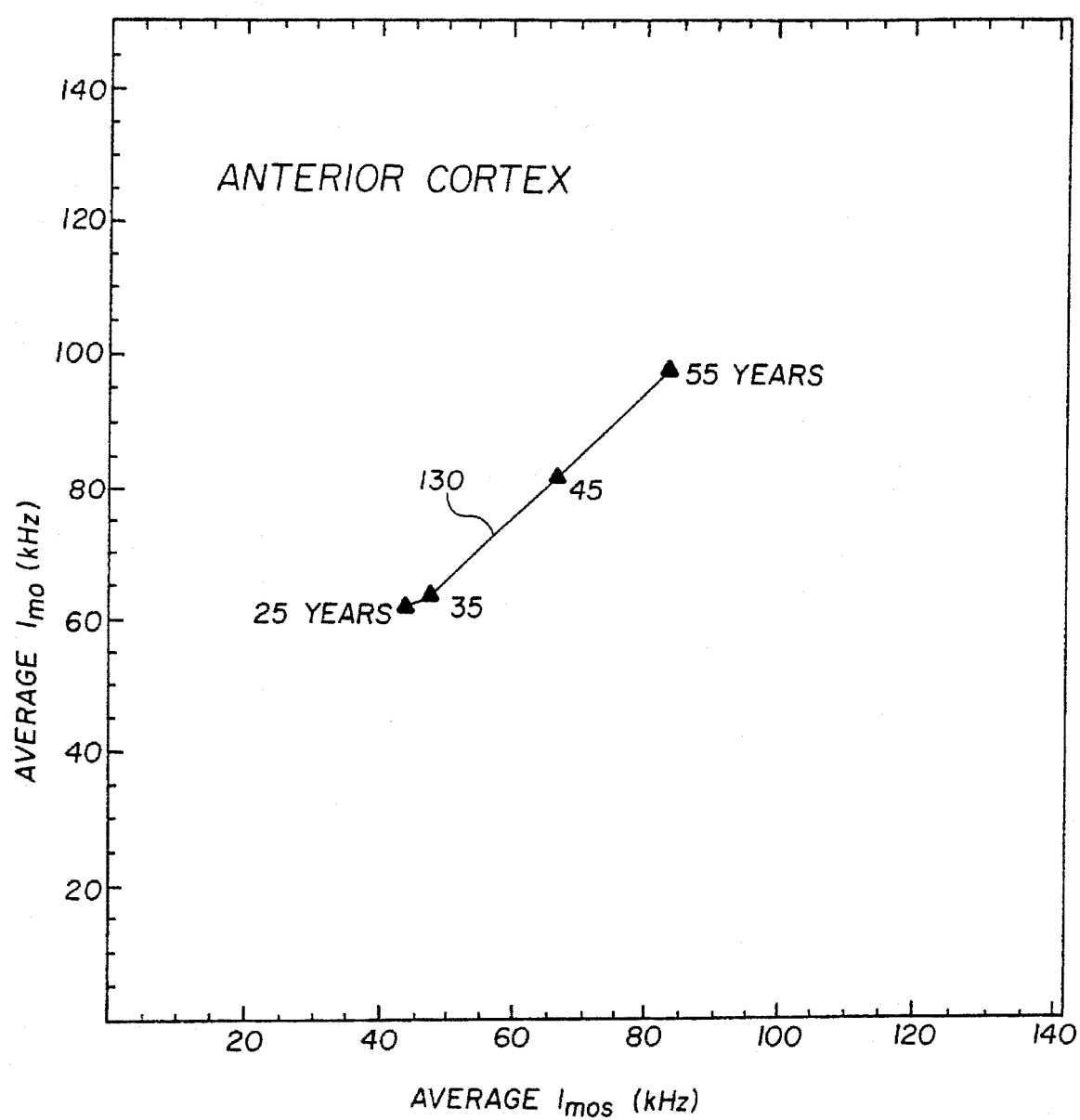
FIG. 8 is a graph of the average intensity of scattering due to mobile particles in the anterior cortex of ocular lenses of subjects with no radiation or steroids, as a function of average intensity of scattering due to slow moving particles and of age group.

FIG. 8 is a graph of average intensity of scattering due to mobile particles in the anterior cortex of ocular lenses of subjects who have not been subjected to radiation treatment or steroids, as a function of-average intensity of scattering due to slow moving particles and of age group. The curve 130 shows that, on average, individuals move farther out along the universal curve (shown in FIG. 7) as they age.

Figure 9:
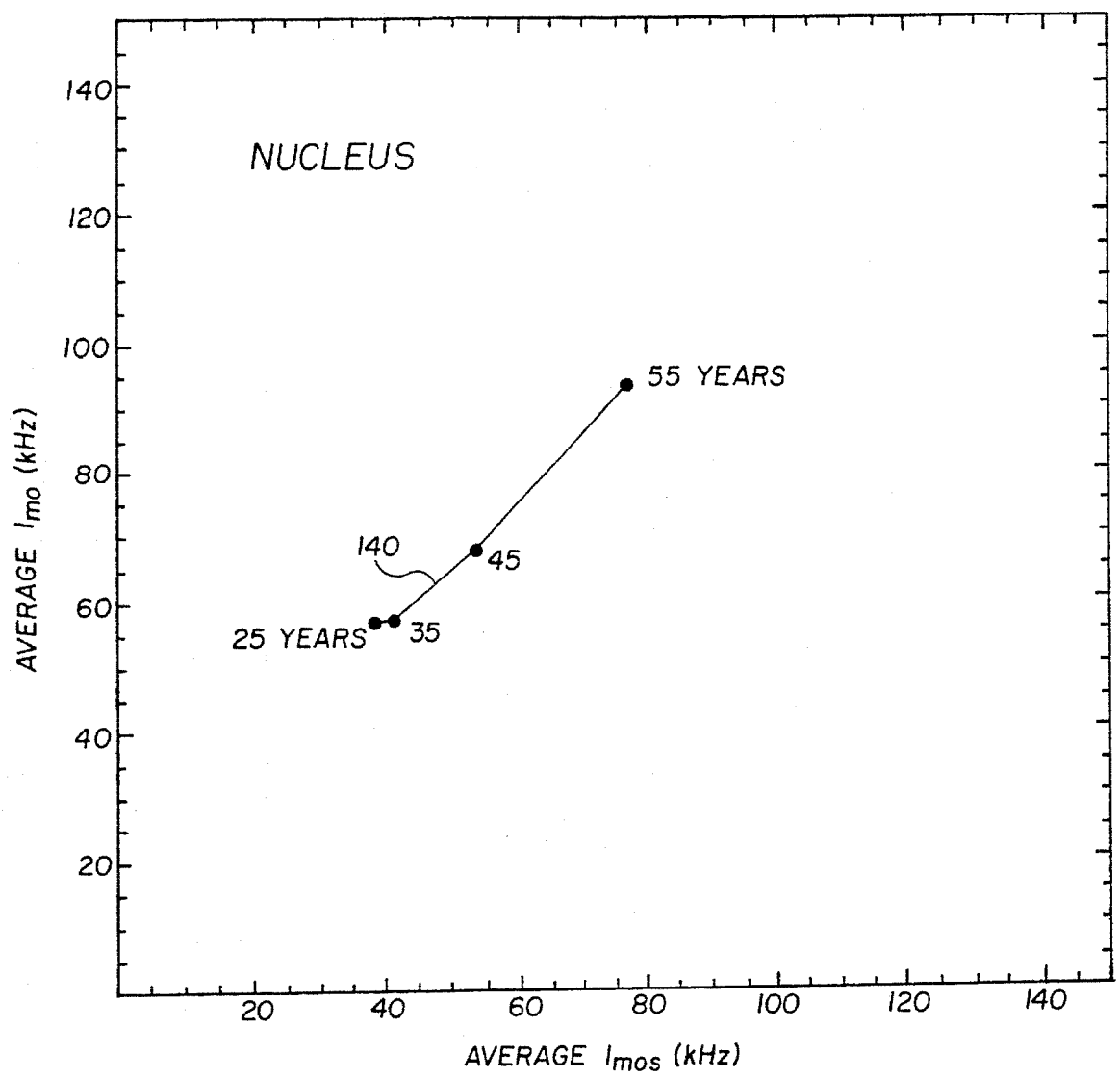
FIG. 9 is a graph of the average intensity of scattering due to mobile particles in the nucleus of ocular lenses of subjects with no radiation or steroids, as a function of average intensity of scattering due to slow moving particles and of age group.

FIG. 9 is a graph of average intensity of scattering due to mobile particles in the nucleus of ocular lenses of subjects who have not been subjected to radiation treatment or steroids, as a function of average intensity of scattering due to slow moving particles and of age group. The curve 140 shows that, on average, individuals move farther out along the universal curve (shown in FIG. 7) as they age.

Figure 10:
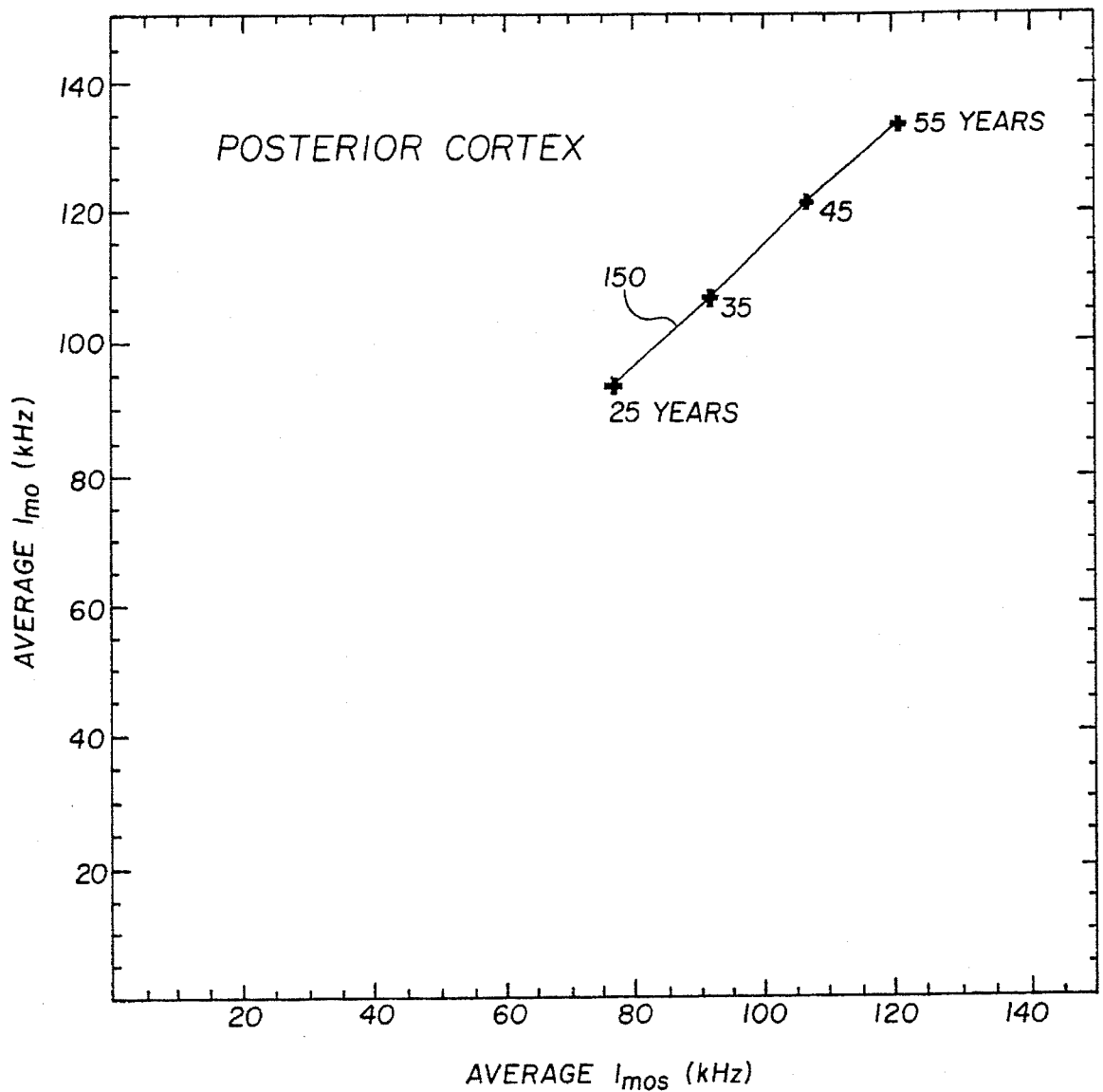
FIG. 10 is a graph of the average intensity of scattering due to mobile particles in the posterior cortex of ocular lenses of subjects with no radiation or steroids, as a function of average intensity of scattering due to slow moving particles and of age group.

FIG. 10 is a graph of average intensity of scattering due to mobile particles in the posterior cortex of ocular lenses of subjects who have not been subjected to radiation treatment or steroids, as a function of average intensity of scattering due to slow moving particles and of age group. The curve 150 shows that, on average, individuals move farther out along the universal curve (shown in FIG. 7) as they age.

Figure 11:
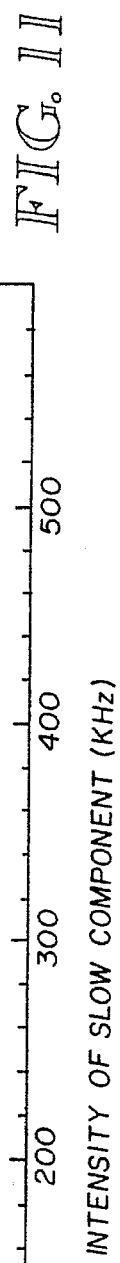
FIG. 11 is a histogram of the intensity of slow components for subjects in a relatively younger age group.
Figure 12:
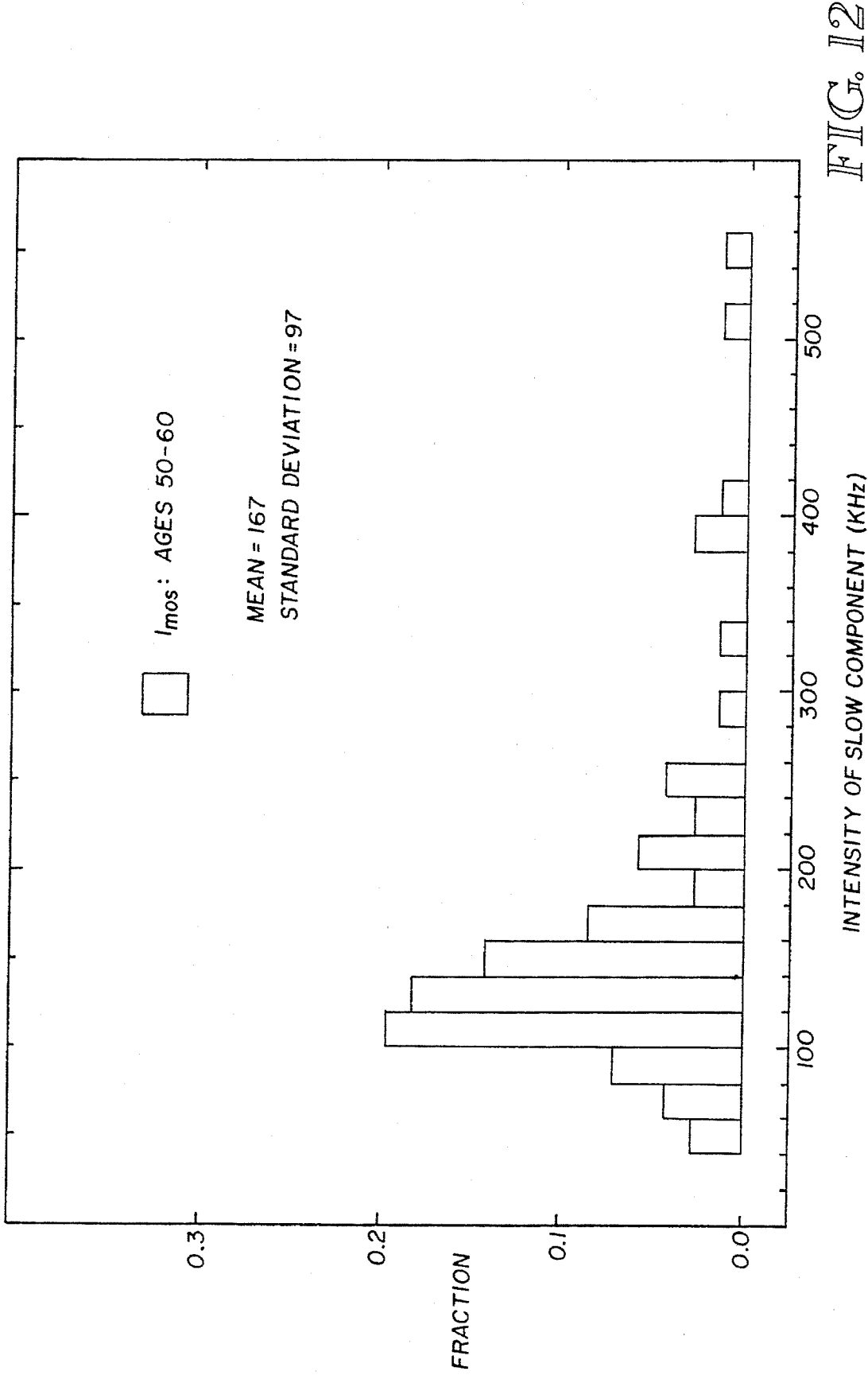
FIG. 12 is a histogram of the intensity of slow components for subjects in a relatively older age group.

FIG. 11 is a histogram of the intensity of slow components for subjects in the age group representing individuals between 20 and 30 years of age. This histogram shows a relatively low average intensity and only a few individuals having significantly higher intensity than the average intensity. FIG. 12 is a histogram of the intensity of slow components for subjects in the age group representing individuals between 50 and 60 years of age. This histogram shows a relatively high average intensity and several individuals having significantly higher intensity than the average intensity. Accordingly, it is possible to detect the presence of cataractogenesis in individuals who are represented by large intensities of scattering due to slow moving particles, relative to the average intensity of scattering for that age group. From our analysis of the population probability distributions of the molecular parameters $I_{mos}$, $\tau_s$, and $I_{imm}$, and of how these probability distributions depend on age, we have discovered that the probability distributions of these parameters have a characteristic form consisting of a sharply peaked central maximum containing most of the measurements, together with a broad tail encompassing individuals who have exhibited anomalously high values of the molecular parameters. Our quantitative findings about the forms of each of these probability distributions are indeed what enable us to identify a given measurement as anomalously high. Thus the position of an individual measurement in the anomalously high region of the probability frequency distribution serves as an indication that the rate of cataractogenesis in that individual has been proceeding at an abnormally rapid rate prior to the measurement.

Figure 13:
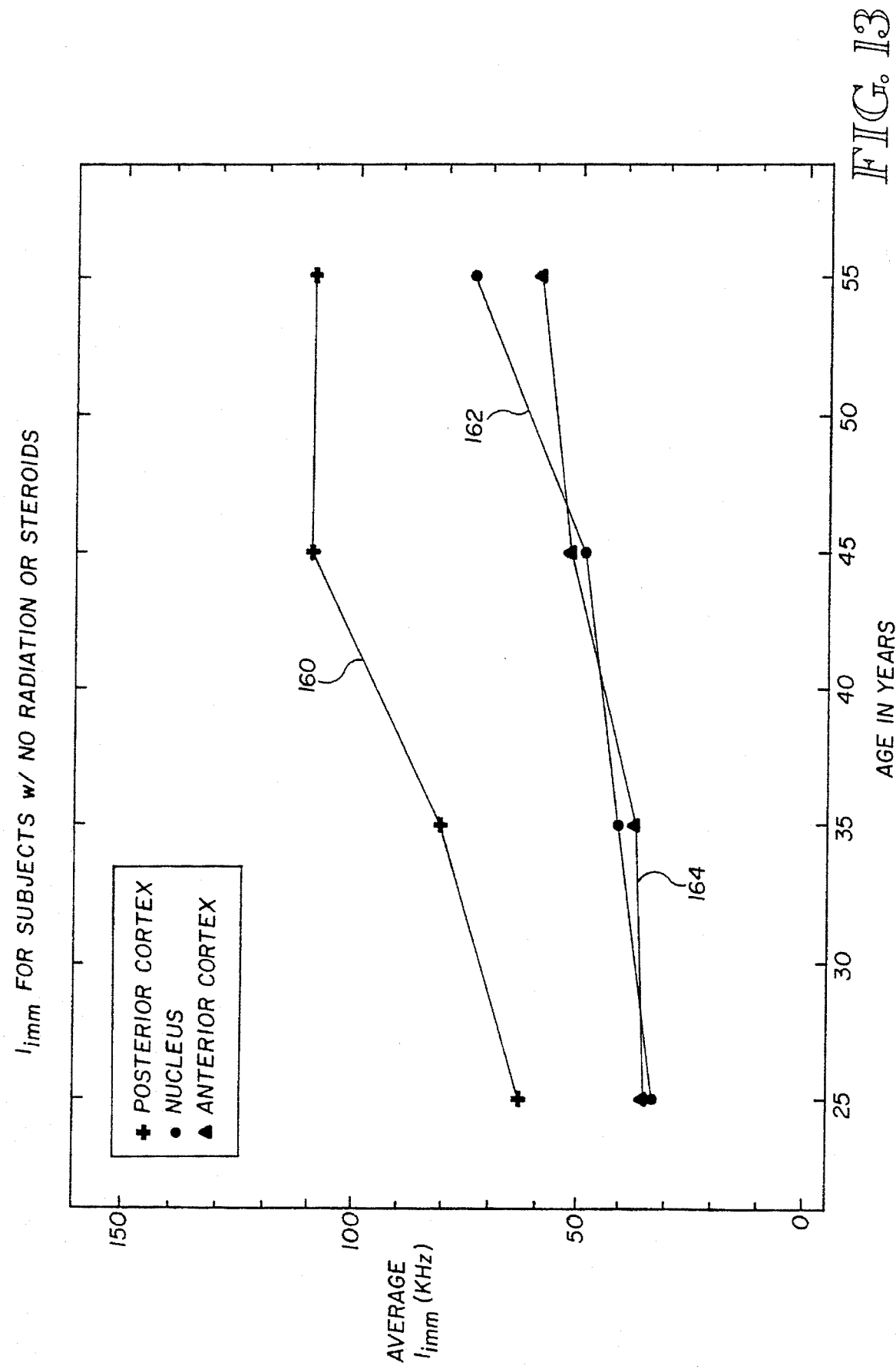
FIG. 13 is a graph of the average intensity of light scattering from immobile particles at various locations in the lens for subjects without radiation or steroids, as a function of age group.

FIG. 13 is a graph of the average intensity of light scattering from immobile particles at various locations in the lens for subjects who have not been subjected to radiation treatment or steroids, as a function of age group. From the curve 160, it is clear that scattering from immobile particles in the posterior cortex of the subjects' eyes is greater than that from the subjects' nucleus (curve 162) or anterior cortex (curve 164). We had previously identified the increased scattering from the slow mobile particles, $I_{mos}$, as a good signature of cataractogenesis. Indeed, $I_{imm}$ is comparable in magnitude to $I_{mos}$. The average value of $I_{imm}$ increases steadily with age, just as the average value of $I_{mos}$ does.

Figure 14:
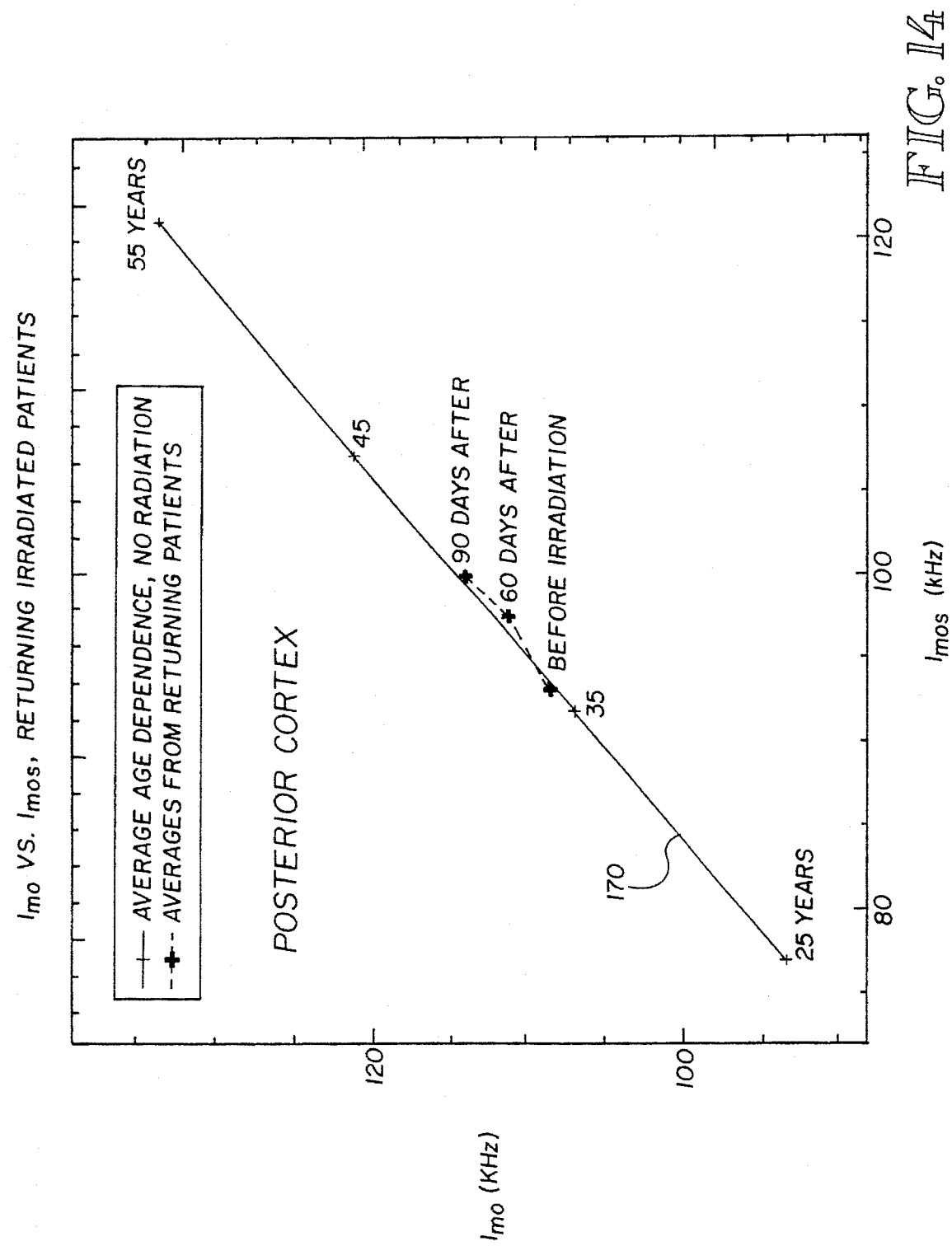
FIG. 14 is a graph of the intensity of light scattering from mobile particles as a function of the intensity of lights scattering from slow moving particles for individuals having no radiation and for individuals having radiation, as a function of time since radiation, in the posterior cortex of the ocular lens.

FIG. 14 is a graph of the intensity of light scattering from mobile particles as a function of the intensity of light scattering from slow moving particles for individuals who have not been subjected to radiation treatment and for individuals having radiation treatment, as a function of time since radiation, in the posterior cortex of the ocular lens. The curve 170 represents the universal curve for the individuals having no radiation treatment. These data indicate that radiation treatment causes data points to move outwardly along the universal curve. These individuals take only 90 days after radiation treatment to move a distance that approximates the change that an untreated person takes six years to experience.

Our data permit the measurement of the average rates of change with age of each of the molecular parameters as a function of position within the ocular lens. The values of the molecular parameters found in an individual patient upon repeated visits will change as a result of the progressive aging and possible cataract formation in that individual's ocular lenses. We are now in a position to compare the rates of change found in a specific individual's lenses with the rates of change to be expected on average for a normal individual as a function of age. By this means, it will be possible to identify anomalously high rates of change of selected molecular parameters. Such high rates of change will be indicative of incipient cataract formation.

Figure 15:
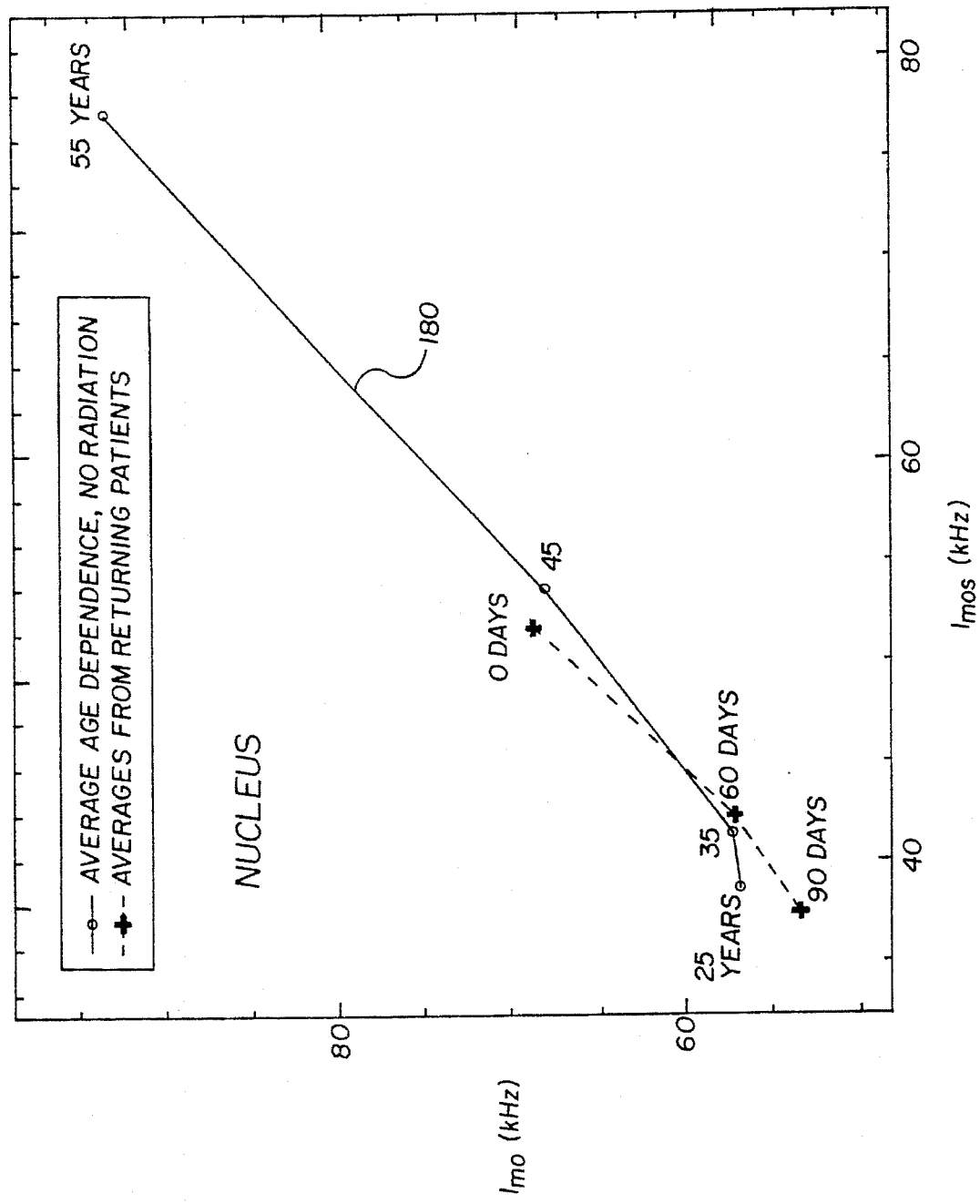
FIG. 15 is a graph of the intensity of light scattering from mobile particles as a function of the intensity of lights scattering from slow moving particles for individuals having no radiation and for individuals having radiation, as a function of time since radiation, in the nucleus of the ocular lens.
Figure 16:
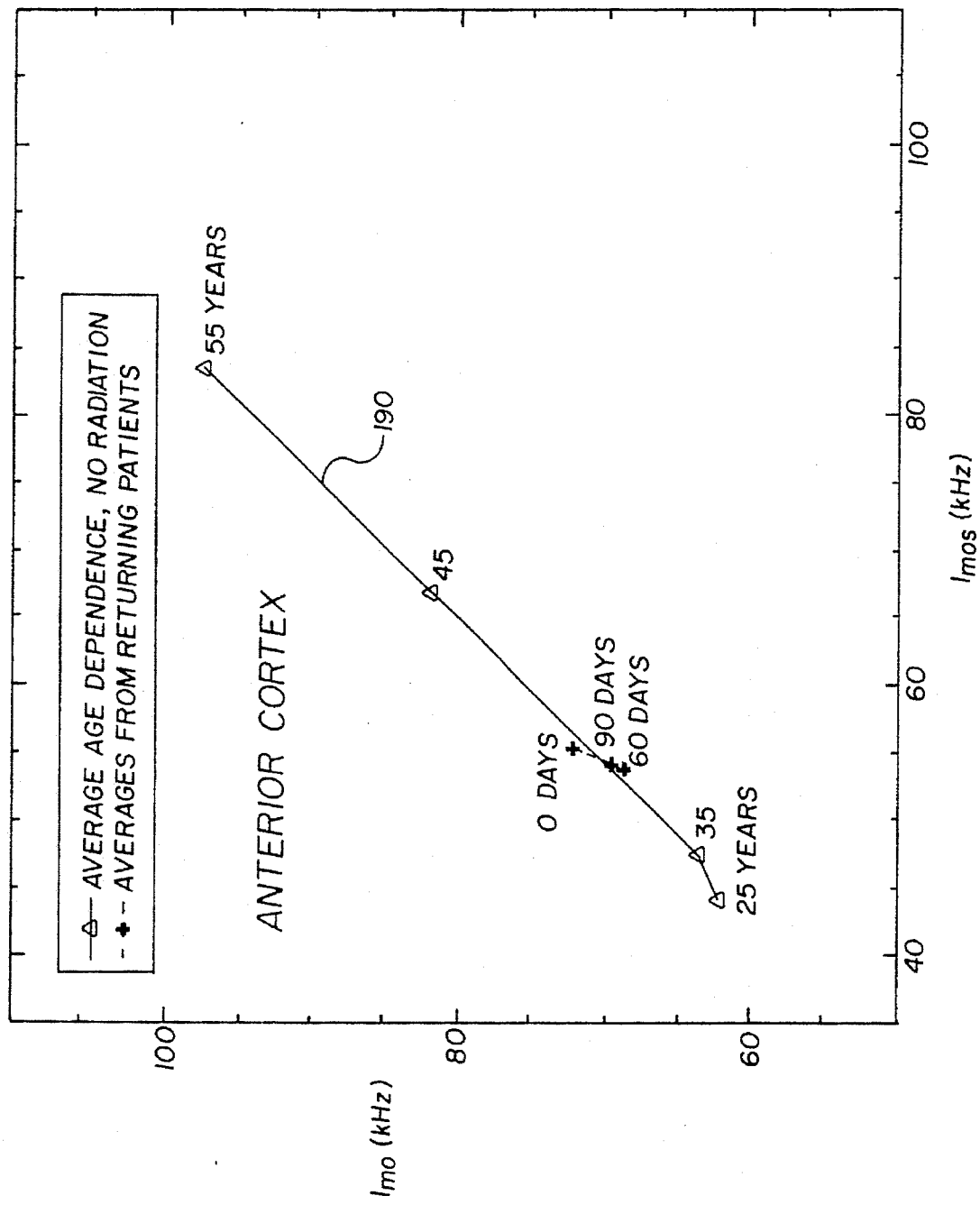
FIG. 16 is a graph of the intensity of light scattering from mobile particles as a function of the intensity of lights scattering from slow moving particles for individuals having no radiation and for individuals having radiation, as a function of time since radiation, in the anterior cortex of the ocular lens.

FIG. 15 is a graph of the intensity of light scattering from mobile particles as a function of the intensity of lights scattering from slow moving particles for individuals who have not been subjected to radiation treatment and for individuals having radiation treatment, as a function of time since radiation, in the nucleus of the ocular lens. The curve 180 represents the universal curve for the individuals having no radiation treatment. These data indicate that radiation treatment causes $I_{mo}$ and $I_{mos}$ for the ocular lens nuclei to move inwardly along the universal curve, contrary to the movement experienced by individuals having no radiation treatment FIG. 16 is a graph of the intensity of light scattering from mobile particles as a function of the intensity of lights scattering from slow moving particles for data points who have not been subjected to radiation treatment and for individuals having radiation treatment, as a function of time since radiation, in the anterior cortex of the ocular lens. The curve 190 represents the universal curve for the individuals having no radiation treatment. These data indicate that radiation treatment does not cause individuals to move significantly along the universal curve.

The computer 70 (see FIG. 1) can be programmed to solve for the intensity of light scattering from mobile ($I_{mo}$) and immobile ($I_{imm}$) scatterers, from the best functional form of the temporal autocorrelation, given in Equation (1), as follows:

The values of $C(0)=\alpha_0 I_{mo}^2 + [I_{mo}+I_{imm}]^2$, and $C(\infty)=[I_{mo}+I_{imm}]^2$ can be determined from the best fitting functional form.

Thus: $I_{mo} = [C(0) - C(\infty)/\alpha_0]^{1/2}$.

Accordingly, since $C(0) = C(0) - C(\infty) +$ $$\left[ \left[ \frac{C(0)-C(\infty)}{\alpha_0} \right]^{1/2} + I_{imm} \right]^2,$$

$$\left[ \frac{C(0)-C(\infty)}{\alpha_0} \right]^{1/2} + I_{imm} = [C(\infty)]^{1/2}, \text{ or}$$

$$I_{imm} = [C(\infty)]^{1/2} - \left[ \frac{C(0)-C(\infty)}{\alpha_0} \right]^{1/2}.$$

The values of $I_{imm}$, $I_{mof}$ and $I_{mos}$ can be solved for in a similar fashion if the temporal autocorrelation function is of the following form:

$$C(\tau)=\alpha_0[I_{mof}exp(-\tau/\tau_f)+I_{mos}exp(-\tau/\tau_s)]^2+[I_{mof}+I_{mos}+I_{imm}]^2.$$

These methods of solution depend upon knowing the value of $\alpha_0$ beforehand. Since it represents scattering in the absence of immobile scatterers, it can be determined in vitro by making temporal autocorrelation function measurements on a solution of polystyrene spheres or on a solution of material isolated from an ocular lens having no immobile scatterers. It can also be estimated in vivo by making temporal autocorrelation measurements on living subjects and choosing as the predetermined valued $\alpha_0$ that value which is the maximum of all of those measured. It is preferable, of course, that the subject for the in vivo evaluation of $\alpha_0$ be chosen from a class which is likely to have a minimum of immobile scatterers in his ocular lens. It has been found that younger individuals are generally preferable to older individuals.

Those skilled in the art will recognize, or be able to ascertain, using no more than routine experimentation, many equivalents to the specific embodiment of the invention described herein. For example, the delivery, observation, control and collection optics are not intended to be solely limited to the embodiments described herein, but rather are intended to extend to any optical system suitable for these purposes. Such equivalents are intended to be encompassed by the following claims.

We claim:

1. Apparatus for in vivo detection of cataractogenesis in ocular tissue, comprising:

a light source producing a substantially monochromatic, coherent, collimated light;

optics coupled to said light source, and directing the light to impinge on the ocular tissue;

a light collector positioned to collect light that is scattered from the ocular tissue, the scattered light having a fluctuating intensity;

analysis electrical circuitry coupled to said collector for performing a mathematical analysis on the intensity and the fluctuations of the intensity of the collected light, thereby determining a signature of cataractogenesis, the signature including an intensity ($I_{imm}$) of the light scattered by immobile scatterers in the ocular tissue; and processing electrical circuitry coupled to said analysis circuitry, and determining from the signature a degree of cataractogenesis.

2. The apparatus of claim 1 wherein the analysis electrical circuitry further computes a temporal autocorrelation function of the fluctuations of the intensity of the collected light.

3. Apparatus for in vivo detection of cataractogenesis in ocular tissue, comprising:

a light source producing a substantially monochromatic, coherent, collimated light;

optics coupled to said light source, and directing the light to impinge on the ocular tissue;

a light collector positioned to collect light that is scattered from the ocular tissue, the scattered light having a fluctuating intensity;

analysis electrical circuitry coupled to said collector for performing a mathematical analysis on the intensity and the fluctuations of the intensity of the collected light to determine a signature of cataractogenesis, the signature including an intensity ($I_{mo}$) of the light scattered by mobile scatterers, and an intensity ($I_{imm}$) of the light scattered by immobile scatterers in the ocular tissue; and processing electrical circuitry coupled to said analysis circuitry, and determining from the signature a degree of cataractogenesis.

4. The apparatus of claim 3 wherein the analysis electrical circuitry further computes a temporal autocorrelation function of the fluctuations of the intensity of the collected light.

5. The apparatus of claim 4 wherein the analysis electrical circuitry further performs a least squares analysis on the temporal autocorrelation function to determine a functional form of the function C(s) which best fits the temporal autocorrelation function, where $$C(\tau)=\alpha_0[I_{mo}f(\tau)]^2+[I_{mo}+I_{imm}]^2,$$

$\tau$ is a time delay variable, $\alpha_0$ is a predetermined constant representative of scattering in an absence of immobile scatterers, and $f(\alpha)$ is a monotonically decreasing positive function in $|\tau|$ and $f(0)=1$ and $f(\tau) \to 0$ as $|\tau| \to \infty$.

6. The apparatus of claim 5, further comprising an apparatus coupled to said analysis circuitry for making measurements of a value of a parameter representative of light scattering from the ocular lens of each member of a population of individuals ;and choosing a value of $\alpha_0$ to be a maximum of the measured values.

7. The apparatus of claim 6, further comprising a calibration apparatus coupled to said analysis circuitry determining a value of $\alpha_0$ from in vitro experimentation in the absence of immobile scatterers.

8. The apparatus of claim 7, further including a calibration solution of polystyrene spheres wherein the calibration apparatus determines said value of $\alpha_0$ comprises electrical circuitry making temporal autocorrelation measurements on said solution of polystyrene spheres.

9. The apparatus of claim 7, further including a calibration solution isolated from an ocular lens containing no immobile scatterers wherein the calibration apparatus determines said value of $\alpha_0$ comprises electrical circuitry making temporal autocorrelation measurements on said calibration solution.

10. Apparatus for in vivo detection of cataractogenesis in ocular tissue, comprising:

a light source producing substantially monochromatic, coherent, collimated light;

optics coupled to said light source, and directing the light to impinge on the ocular tissue;

a light collector constructed to collect light that is scattered from the ocular tissue;

analysis electrical circuitry coupled to said collector for performing a correlation analysis on the collected light to determine a signature of cataractogenesis, the signature including an intensity ($I_{mof}$) of the light scattered by fast moving scatterers, a diffusion decay time ($\tau_f$) of fast moving scatterers, an intensity ($I_{mos}$) of the light scattered by slow moving scatterers, a diffusion decay time ($\tau_s$) of slow moving scatterers, and an intensity ($I_{imm}$) of the light scattered by immobile scatterers in the ocular tissue; and processing electrical circuitry coupled to said analysis circuitry and determining from the signature a degree of cataractogenesis.

11. The apparatus of claim 10 wherein the analysis electrical circuitry comprises a computer programmed to compute a temporal autocorrelation function of the intensity of the collected light.

12. The apparatus of claim 10 wherein the analysis electrical circuitry comprises an integrated circuit for computing a temporal autocorrelation function of the intensity of the collected light.

13. The apparatus of claim 10 wherein the analysis electrical circuitry comprises a standalone autocorrelator for computing a temporal autocorrelation function of the intensity of the collected light.

14. The apparatus of claim 10 wherein the analysis electrical circuitry further performs a least squares analysis on a temporal autocorrelation function to determine a functional form of the function C(s) which best fits the temporal autocorrelation function, where $$C(\tau)=\alpha_0[I_{mof}exp(-\tau/\tau_f)+I_{mos}exp(-\tau/\tau_s)]^2+[I_{mof}+I_{mos}+I_{imm}]^2,$$

$\tau$ is a time delay variable, and $\alpha_0$ is a predetermined constant representative of scattering in an absence of immobile scatterers.

15. The apparatus of claim 14 further comprising measurement electrical circuitry coupled to said analysis circuitry and making measurements of a value of a parameter representative of light scattering from the ocular lens of each member of a population of individuals and choosing a value of $\alpha_0$ to be a maximum of the measured values.

16. The apparatus of claim 14, further comprising a calibration apparatus coupled to said analysis circuitry for determining a value of $\alpha_0$ from in vitro experimentation in the absence of immobile scatterers.

17. The apparatus of claim 15, further including a calibration solution of polystyrene spheres wherein the calibration apparatus determines said value of $\alpha_0$ comprises means for making correlation measurements on a solution of polystyrene spheres.

18. The apparatus of claim 15, further including a calibration solution isolated from an ocular lens containing no immobile scatterers wherein the calibration apparatus for determining a value of $\alpha_0$ comprises means for making correlation measurements on said calibration solution.

19. Apparatus for in vivo detection of cataractogenesis in ocular tissue of an individual subject, comprising:

a light source producing substantially monochromatic, coherent, collimated light;

optics coupled to said light source, and directing the light to impinge on the individual subject's ocular tissue;

a light collector positioned to collect light that is scattered from the individual subject's ocular tissue;

analysis electrical circuitry coupled to said collector for performing a correlation analysis on the collected light to determine values of variables, including an intensity ($I_{mo}$) of the light scattered by the slow moving scatterers in the subject's ocular tissue, and an intensity ($I_{imm}$) of the light scattered by immobile scatterers in the ocular tissue;

processing electrical circuitry coupled to said analysis circuitry to develop a frequency distribution of at least one of the variables based on values of the variables for a population of subjects; and means coupled to said processing circuitry for determining a rate of cataractogenesis for the individual subject, by comparing the value of at least one variable for the individual subject to the frequency distribution for the at least one variable.

20. The apparatus of claim 19 wherein the processing electrical circuitry develops the frequency distribution of exactly one of the variables.

21. Apparatus for in vivo detection of cataractogenesis in ocular tissue of an individual subject, comprising:

apparatus for analyzing the ocular tissue of the individual subject at a first time and at a second time that is different from the first time, the apparatus including:

a light source for producing substantially monochromatic, coherent, collimated light;

optics coupled to said light source, and directing the light to impinge on the ocular tissue of the individual subject;

a light collector positioned to collect light that is scattered from the ocular tissue of the individual subject; and analysis electrical circuitry coupled to said collector for performing a correlation analysis on the collected light to determine values of variables, including an intensity ($I_{mo}$) of the light scattered by mobile scatterers, and an intensity ($I_{imm}$) of the light scattered by immobile scatterers in the ocular tissue of the subject;

apparatus coupled to said analysis circuitry for determining a rate of change of at least one of the variables of the individual subject's ocular tissue as a function of age;

means coupled to said-analysis circuitry for analyzing the ocular tissue of each individual in a population of individuals at a third time, including:
  storage means, coupled to said analysis circuitry, for storing the values of the variables determined by the analysis circuitry and associating those values with a particular individual subject and point in time; and comparison electrical circuitry coupled to said analysis circuitry and said storage means to compare a rate of change of the at least one variable for the particular individual subject to the normal value of a rate of change with age of the at least one variable for the population of subjects to detect cataractogenesis in the ocular tissue of the individual subject.

* * * * *

UNITED STATES PATENT AND TRADEMARK OFFICE
CERTIFICATE OF CORRECTION

PATENT NO.    : 5,540,226
DATED         : July 30, 1996
INVENTOR(S)   : George M. Thurston et al.

It is certified that error appears in the above identified patent and that said Letters Patent is hereby corrected as shown below:

In column 11, line 38, please delete "τis" and insert therefor --τ is--.

In column 11, line 40, please delete "α" and insert therefor --τ--.

In column 11, line 46, before "and", please delete ";".

In column 11, line 47 please delete "6" and insert therefor --5--.

In column 12, line 37 following "14", please insert --,--.

In column 12, line 47 please delete "15" and insert therefor --16--.

In column 12, line 52 please delete "15" and insert therefor --16--.

Signed and Sealed this

Twenty-second Day of October, 1996

Attest:

BRUCE LEHMAN

*Attesting Officer*     *Commissioner of Patents and Trademarks*